US008157798B2

(12) United States Patent
Takahashi

(10) Patent No.: US 8,157,798 B2
(45) Date of Patent: Apr. 17, 2012

(54) TREATMENT TOOL FOR ENDOSCOPE

(75) Inventor: Ichiro Takahashi, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 1075 days.

(21) Appl. No.: 11/796,785

(22) Filed: Apr. 30, 2007

(65) Prior Publication Data

US 2008/0033238 A1    Feb. 7, 2008

(30) Foreign Application Priority Data

Jun. 7, 2006 (JP) ................ P2006-158614

(51) Int. Cl.
*A61B 18/12* (2006.01)
(52) U.S. Cl. .................. 606/47; 606/46; 600/102
(58) Field of Classification Search .......... 606/46, 606/47, 113; 600/102, 104, 106
See application file for complete search history.

(56) References Cited

U.S. PATENT DOCUMENTS

| 3,955,578 | A | * | 5/1976 | Chamness et al. | 606/47 |
| 4,696,544 | A | * | 9/1987 | Costella | 385/118 |
| 5,066,295 | A | * | 11/1991 | Kozak et al. | 606/47 |
| 5,984,920 | A | | 11/1999 | Steinbach | |
| 6,221,007 | B1 | * | 4/2001 | Green | 600/160 |
| 6,235,026 | B1 | * | 5/2001 | Smith | 606/46 |
| 7,008,420 | B2 | * | 3/2006 | Okada | 606/47 |
| 7,198,599 | B2 | * | 4/2007 | Goto et al. | 600/154 |
| 7,758,593 | B2 | * | 7/2010 | Nobis et al. | 606/113 |
| 2003/0109874 | A1 | * | 6/2003 | Dennis | 606/47 |

FOREIGN PATENT DOCUMENTS

| JP | 11-114059 | 4/1999 |
| JP | 2002-224120 | 8/2002 |
| JP | 2003-339731 | 12/2003 |
| JP | 2004-141486 | 5/2004 |
| JP | 2004-513740 | 5/2004 |
| JP | 2005-198735 | 7/2005 |
| JP | 2005-279126 | 10/2005 |
| WO | WO 00/42926 | 7/2000 |
| WO | 02/41793 A1 | 5/2002 |

OTHER PUBLICATIONS

Japanese Official Action dated Mar. 9, 2010 together with an English language translation.
Japanese Official Action dated Apr. 26, 2011 together with an English language translation.
Japanese Office Action dated Jun. 14, 2011 from corresponding Japanese Patent Application No. 2006-158614 together with English language translation.

* cited by examiner

*Primary Examiner* — Michael Peffley
(74) *Attorney, Agent, or Firm* — Scully, Scott, Murphy & Presser, P.C.

(57) ABSTRACT

A treatment tool for an endoscope includes: a treatment portion that is positioned on a distal end side and of which at least a portion is formed from an electroconductive material; an operating wire that is formed from an electroconductive material and is connected to the treatment portion; a sheath that is formed from an electrically non-conductive material through which the operating wire is inserted; a base that is fixed to a base end side of the sheath; an operating section that is rotatably mounted on the base and is connected to a base end side of the operating wire, and that causes the treatment portion to move forwards and backwards and to rotate via the operating wire; and a plug that is provided on the base and is electrically connected to the operating wire.

6 Claims, 14 Drawing Sheets

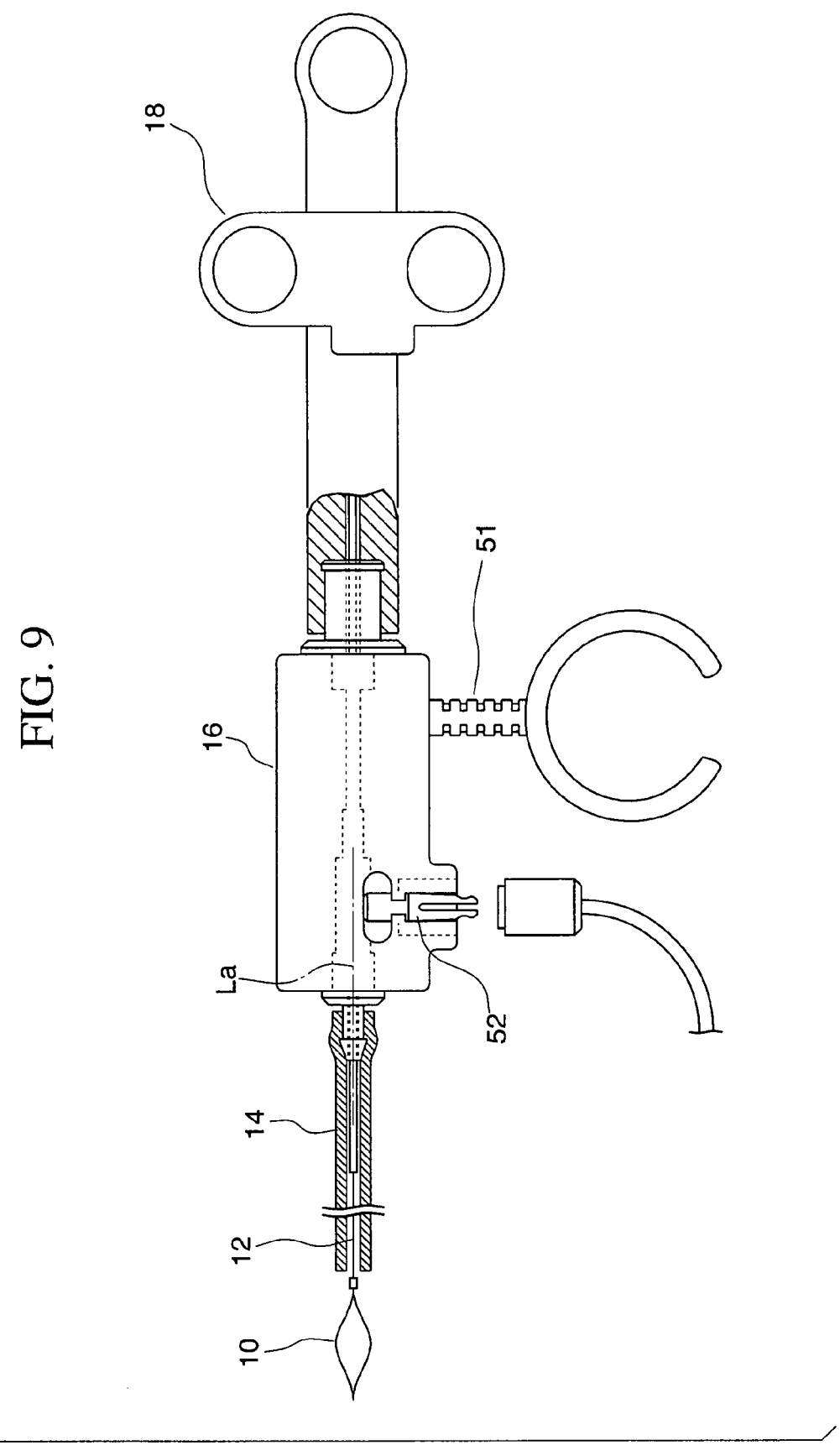

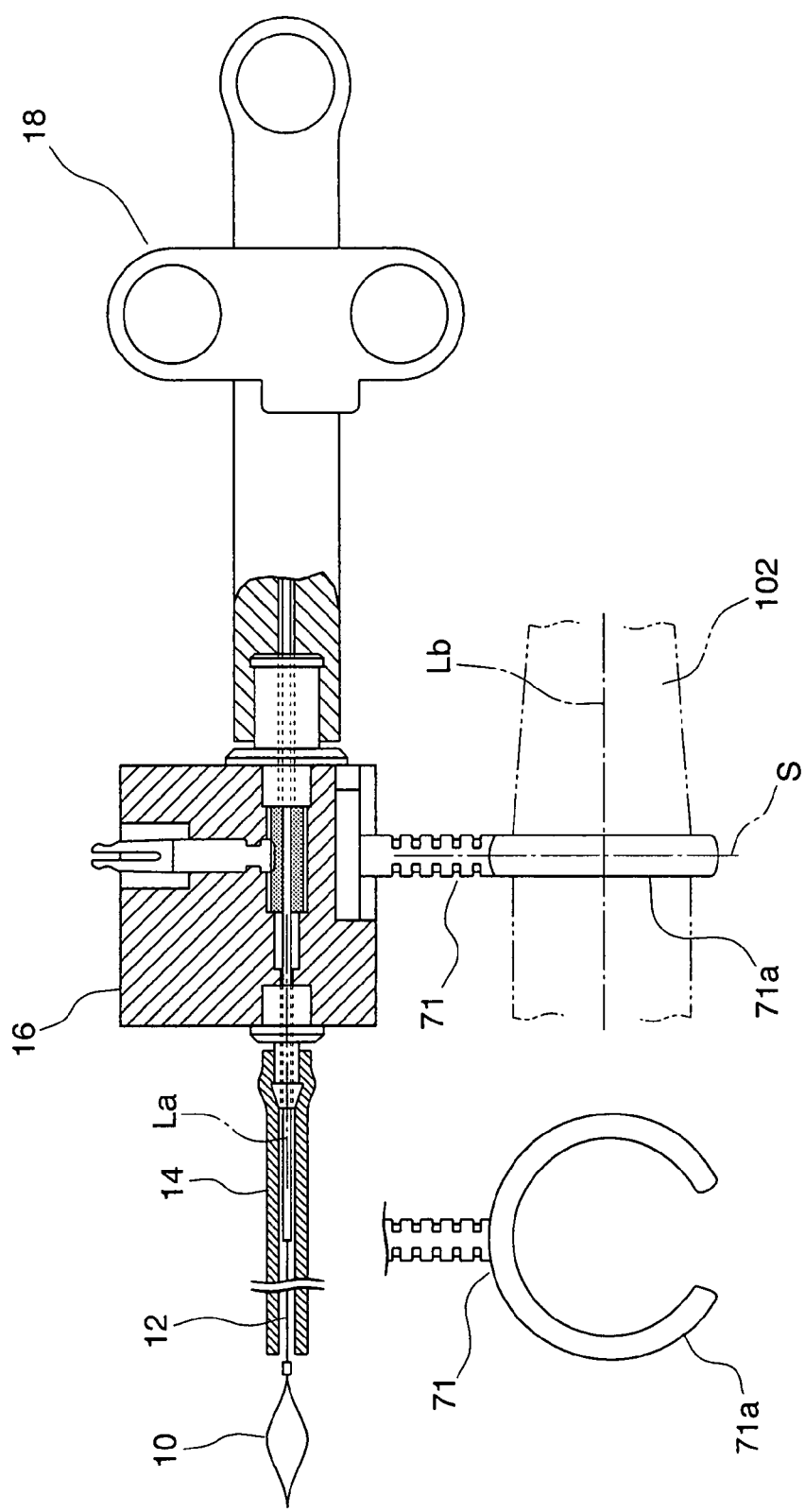

TREATMENT TOOL FOR ENDOSCOPE

TECHNICAL FIELD

The present invention relates to a treatment tool for an endoscope that is inserted into a body through a channel in an endoscope and performs treatments such as excising tissue or cells in predetermined portions of the body.

Priority is claimed on Japanese Patent Application No. 2006-158614, filed Jun. 07, 2006, the contents of which are incorporated herein by reference.

BACKGROUND ART

Treatment tools for an endoscope include those that supply a high frequency current from an operating section positioned adjacent to an operator to a treatment portion positioned at a distal end of the endoscope via an operating wire in order to perform treatments such as stopping bleeding from body tissue or cells, burning, or suturing or incising tissue or the like.

When using this type of treatment tool for an endoscope, not only is the operating wire moved forwards or backwards in an axial direction via the operating section, but the operating wire may also be made to rotate around its axis from the operators side. This is in order that the treatment tool at the distal end can be made to touch tissue or cells inside a body at the optimum attitude, or in order that the optimum portion of the treatment tool at the distal end can be made to touch the tissue or cells.

In Patent Document 1 (Japanese Unexamined Patent Application, First Publication No. 2005-198735), an operating dial portion that can be moved freely forwards and backwards and can also rotate freely is placed on the main body of the operating section, and a connecting pin that is electrically connected to the operating wire is attached to a protruding portion on the base end side of the operating dial portion. A connecting cord that is used to supply high frequency current is electrically connected to this connecting pin.

DISCLOSURE OF INVENTION

An object of the present invention is to provide a treatment tool for an endoscope that has excellent operability when making a forward or backward movement or a rotational movement without the connecting cord which is connected to a plug getting in the way, and that, additionally, can be operated using only one hand.

The present invention employs the following device.

The treatment tool for an endoscope of the present invention includes: a treatment portion that is positioned on a distal end side and of which at least a portion is formed from an electroconductive material; an operating wire that is formed from an electroconductive material and is connected to the treatment portion; a sheath that is formed from an electrically non-conductive material through which the operating wire is inserted; a base that is fixed to a base end side of the sheath; an operating section that is rotatably mounted on the base and is connected to a base end side of the operating wire, and that causes the treatment portion to move forwards and backwards and to rotate via the operating wire; and a plug that is provided on the base and is electrically connected to the operating wire.

BRIEF DESCRIPTION OF THE DRAWINGS

FIG. 9 is a partial cross-sectional view showing a treatment tool for an endoscope according to a third embodiment of the present invention.

FIG. 12 is a partial cross-sectional view showing a treatment tool for an endoscope according to a fifth embodiment of the present invention.

BEST MODE FOR CARRYING OUT THE INVENTION

Respective embodiments of the present invention will now be described.

[First Embodiment]

FIGS. 1 through 6 show a treatment tool for an endoscope according to a first embodiment of the present invention.

Figure 1:
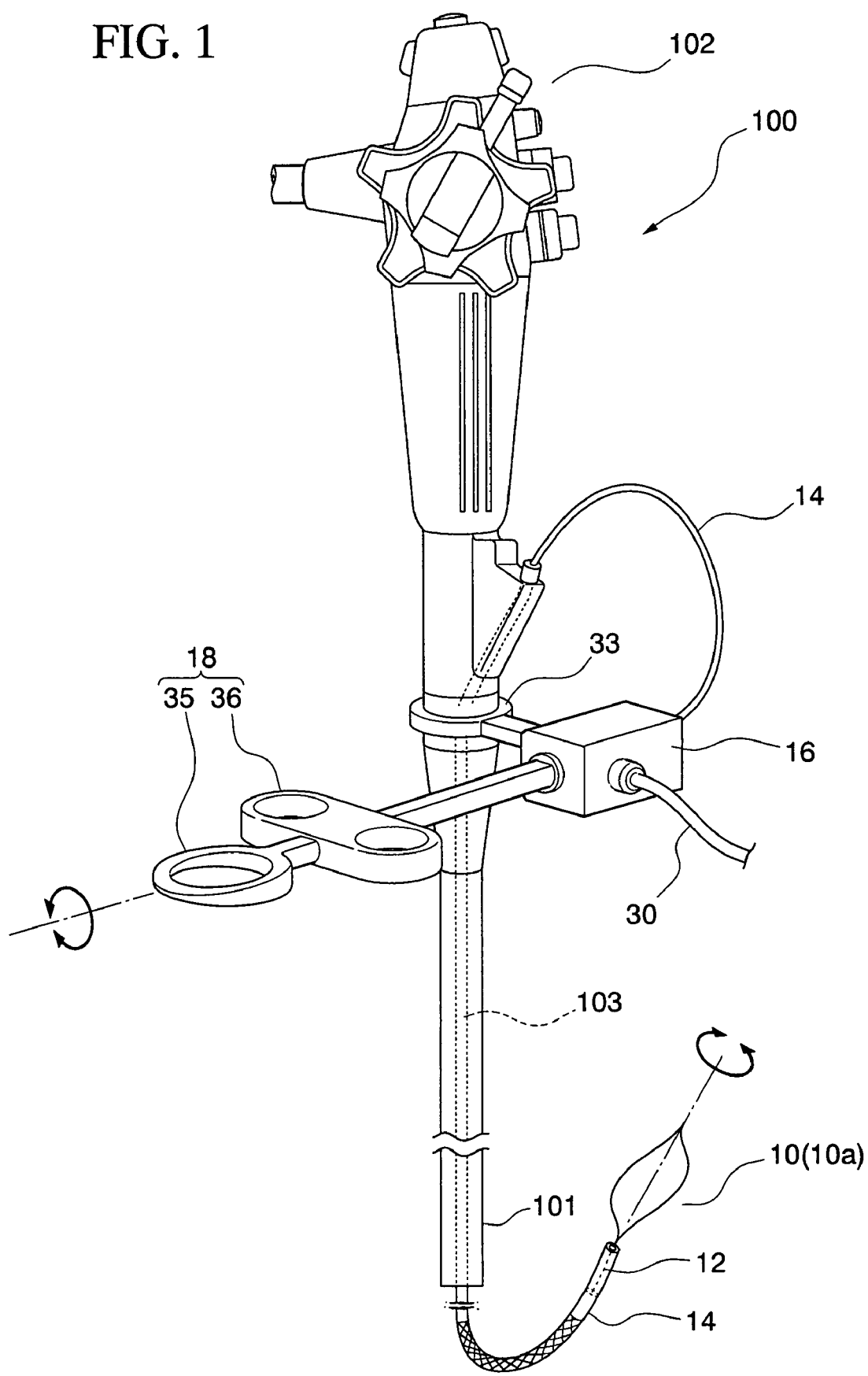
FIG. 1 is a perspective view showing a state in which a treatment tool for an endoscope according to a first embodiment of the present invention is assembled with an endoscope.

In FIG. 1, the symbol 100 indicates an endoscope. The endoscope 100 is provided with an endoscope insertion portion 101 that is inserted into a body, and an operating section 102 that is provided at a base end of the endoscope insertion portion 101 and bends a distal end portion of the endoscope insertion portion 101. A channel 103 is opened in the operating section 102 of the endoscope, and a treatment tool 1 for an endoscope according to the present embodiment is inserted inside the channel 103 via an aperture portion.

Figure 2:
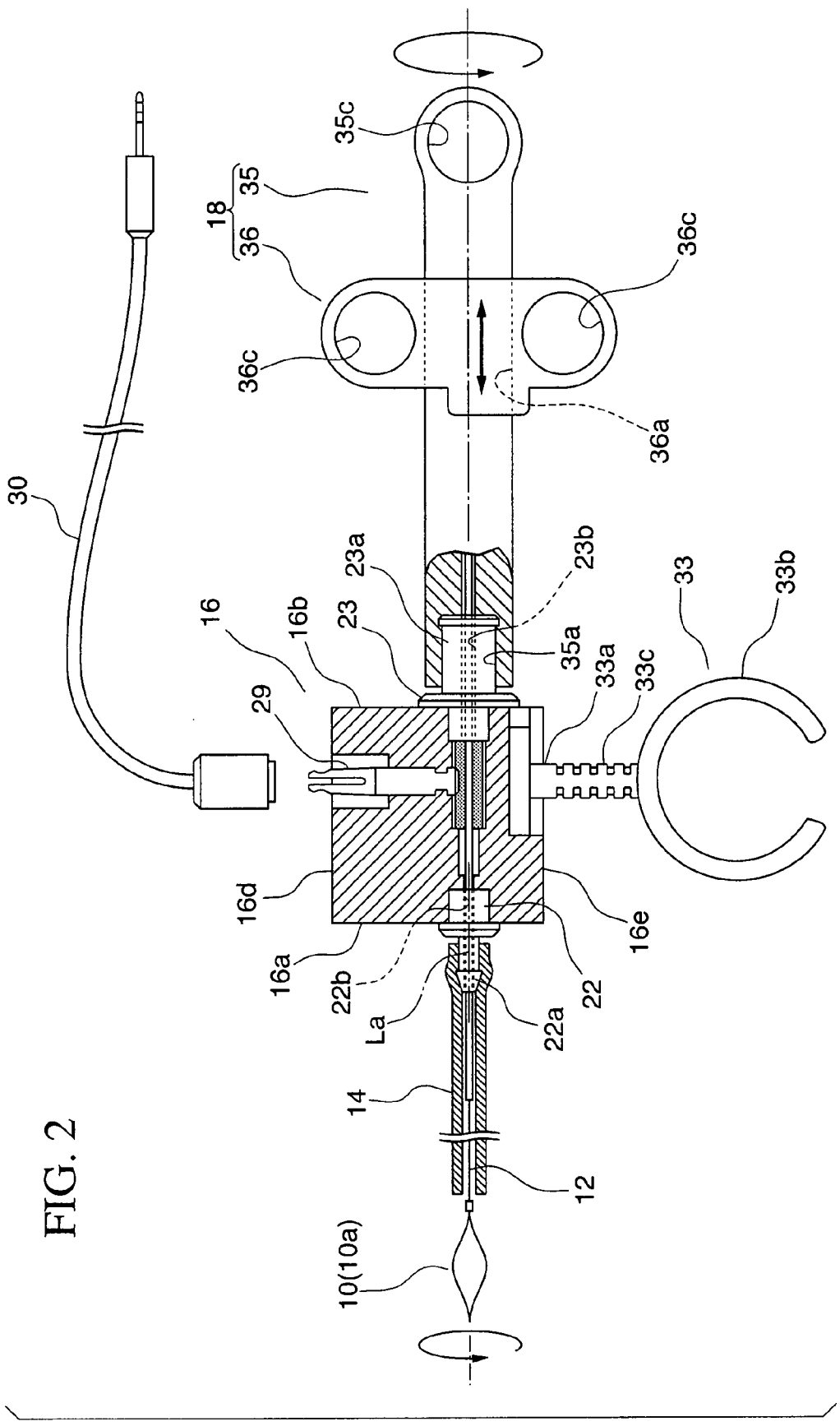
FIG. 2 is a partial cross-sectional view showing the treatment tool for an endoscope according to the first embodiment of the present invention.

As is shown n FIG. 2, the treatment tool 1 for an endoscope is provided with a treatment portion 10 that is located at a distal end side and of which at least a portion is formed from an electroconductive material, an operating wire 12 that is formed from an electroconductive material and is electrically and mechanically connected to the treatment portion 10, a sheath 14 through which the operating wire 12 is inserted, a base 16 that is fixed to the base end side of the sheath 14, and an operating section 18 that is rotatably mounted on the base 16 and is connected to the base end side of the operating wire 12, and that causes the treatment portion 10 to move forwards and backwards and to rotate via the operating wire 12.

In FIGS. 1 and 2, an example is shown in which a snare 10a is used as a treatment tool, however, the treatment tool to which the present embodiment can be applied is not limited to the snare 10a, and may also be, for example, an L-shaped high frequency scalpel. If necessary, a treatment tool may also be used that can be moved forwards and backwards and be rotated by the operating wire 12, and that receives the supply of high frequency current and performs predetermined treatment on a portion being treated.

The sheath 14 is formed by a tube made from a material that is electrically non-conductive and has flexibility such as, for example, polytetrafluoroethylene.

Figure 4:
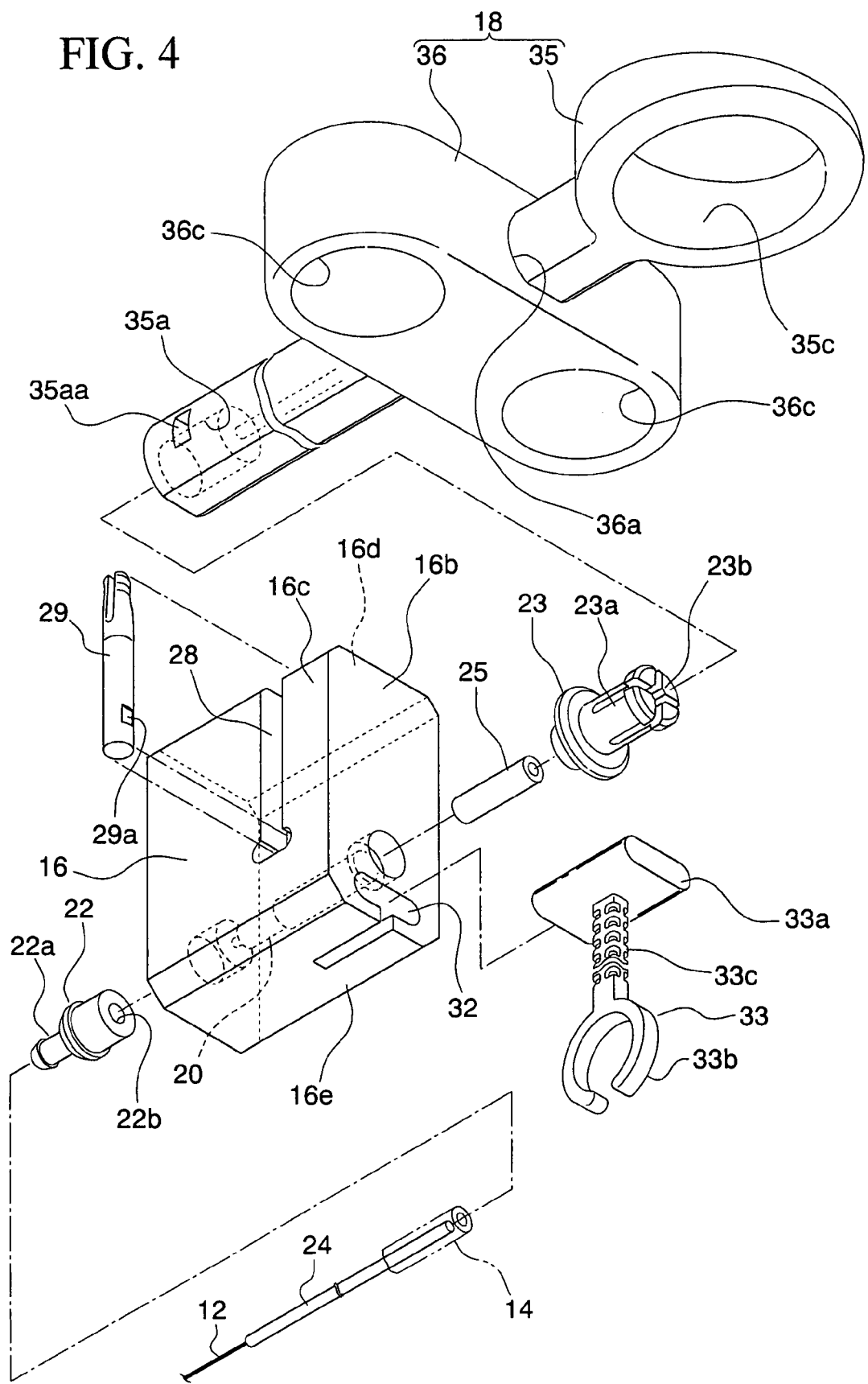
FIG. 4 is an exploded perspective view showing principal portions of the treatment tool for an endoscope according to the first embodiment of the present invention.

As is shown in FIG. 4, the base 16 has a rectangular parallelepiped-shaped exterior, and a through hole 20 through which the operating wire 12 is passed is formed inside the base 16 so as to extend from one side surface 16a of the base 16 to another side surface 16b thereof. A connecting component 22 is fixed to an aperture portion on the one side surface 16a side of the through hole 20. When the connecting component 22 is fixed to the base 16, a protruding portion 22a that protrudes from the base 16 is fixed to a base end portion of the sheath 14 by a suitable fixing device such as an adhesive agent. In contrast, an engaging component 23 is fixed to an aperture portion on the other side surface 16b side of the through hole 20. When the engaging component 23 is fixed to the base 16, a protruding end portion 23a that is divided into four parts and protrudes from the base 16 is rotatably engaged in an engaging hole 35a of an operating section main body 35 (described below).

Note that the connecting component 22 and the engaging component 23 may also be formed integrally with the base 16.

Through holes 22b and 23b are formed respectively in the connecting component 22 and the engaging component 23. The operating wire 12 and a metal operating pipe 24 that is fitted externally onto the operating wire 12 pass through the through holes 22b and 23b.

Figure 3:
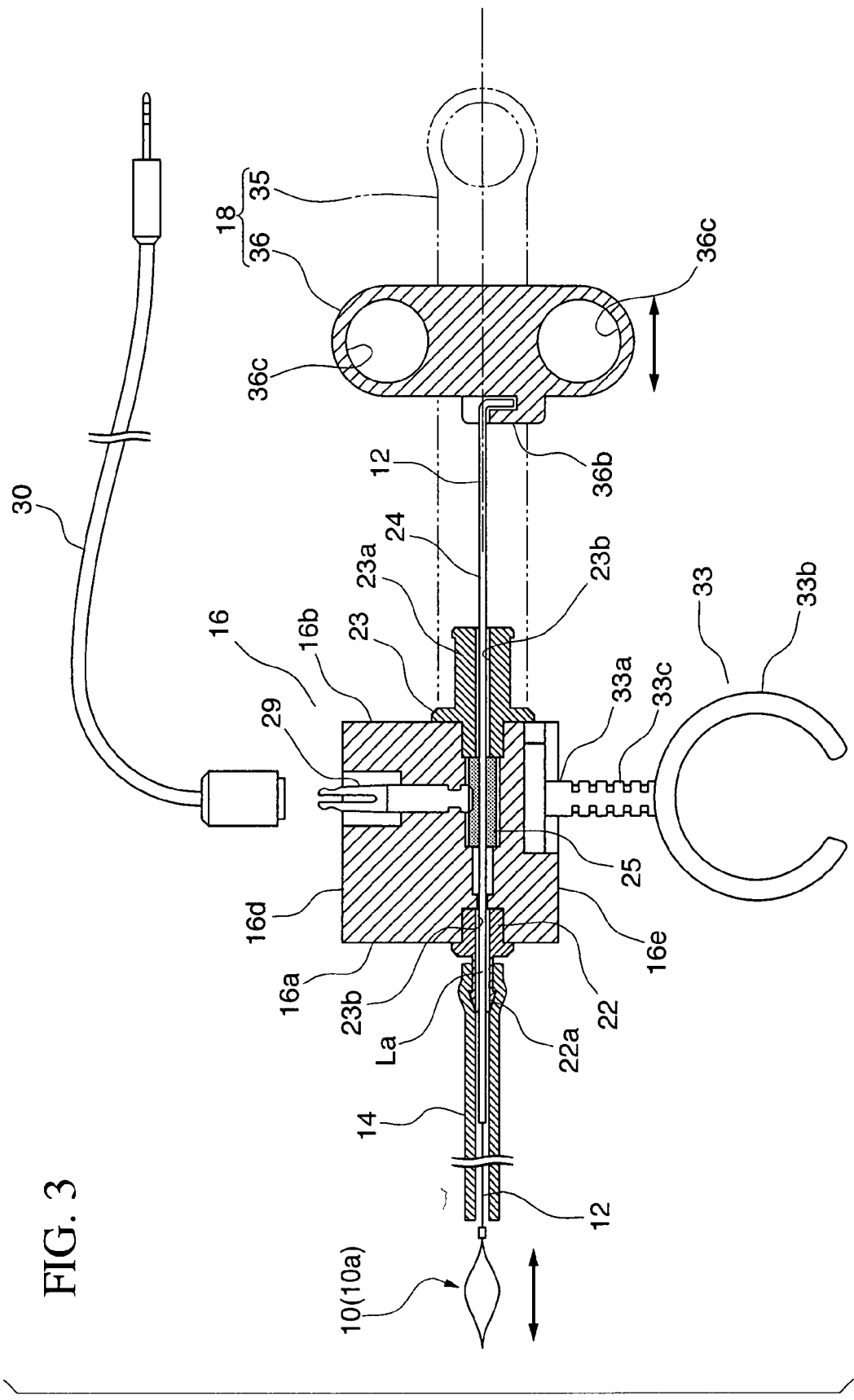
FIG. 3 is a partial cross-sectional view showing the treatment tool for an endoscope according to the first embodiment of the present invention.

Moreover, as is also shown in FIG. 3, when the operating wire 12 and the operating pipe 24 are to be inserted through the through hole 20, a cylindrical component 25 that has suitable elasticity and is formed from an electroconductive material is fitted over the external circumference of the operating pipe 24.

A plug insertion groove 28 is formed in the base 16 so as to extend from a top surface 16c as far as a position partway towards a bottom surface thereof, and a bottom end portion of the plug insertion groove 28 is formed so as to communicate with the through hole 20. A plug 29 is set in this plug insertion groove 28 by being inserted therein such that a distal end thereof protrudes from an end surface 16d of the base. When the plug 29 is set by being inserted into the plug insertion groove 28, then as a result of a projection on the base 16 side being engaged in an anchoring groove 29a that is formed in a side portion of the plug 29, movement of the plug 29 in a longitudinal direction is restricted. In addition, the cylindrical component 25 that has been fitted onto the external circumference of the operating pipe 24 is pushed at a predetermined pressure by the base end portion of the plug 29 which has been set in a normal position towards the operating wire 12 side that is placed at a predetermined position in the center of the base 16. As a result of this, the plug 29, the cylindrical component 25, the operating pipe 24, and the operating wire 12 are mutually electrically connected inside the base 16.

Note that the plug 29 is electrically connected to a high frequency power supply (not shown) via a connecting cord 30.

Moreover, an attachment engaging groove 32 is formed in the base 16 so as to extend from the other side surface 16b in parallel with the axis of the through hole 20 as far as a position in the center of the base 16. Note that the attachment engaging groove 32 also opens onto an end surface 16e of the base. As a result of a base end portion 33a of an attachment 33 being engaged in the attachment engaging groove 32, the attachment 33 is set in the attachment engaging groove 32 such that the axis thereof is coaxial with the plug 29, and such that the attachment 33 protrudes from the base 16 in the opposite direction from the plug 29. A C-shaped engaging ring 33b is formed on a distal end of the attachment 33 and the attachment 33 is able to be anchored on a bottom end portion of the endoscope operating section 102 via this engaging ring 33b.

Note that a weaker portion 33c is provided on the base portion side with respect to the engaging ring 33b of the attachment 33. When an external force is applied between the base 16 and the endoscope operating section 102, the weaker portion 33c is suitably deformed so that the operating section 18 can be operated in a suitable position. Moreover, because excessive force is not applied to the base 16 or the endoscope operating section 102, the attachment 33 can be prevented from becoming unattached from the endoscope operating section 102.

The operating section 18 is provided with an operating section main body 35 that is rotatably mounted via the engaging component 23 on the opposite side from the sheath 14 of the base 16, and a slider 36 that is mounted such that it can move forwards and backwards along the operating section main body 35.

The operating section main body 35 is formed having an overall elongated shape in which the cross section of the principal portion is substantially rectangular. By inserting the protruding end portion 23a, which is divided into four parts, of the engaging component 23 into the hole 35a that is formed in the base end portion of the operating section main body 35, the operating section main body 35 is mounted coaxially with a base end side axis La of the sheath 14 and so as to be able to rotate around this same axis La, in other words, rotate around the axis of the through hole 20.

Note that an engaging hole 35aa a is formed in both side surfaces of a base end portion of the operating section main body 35, and a large diameter portion of the protruding end portion 23a, which has been divided into four parts, of the engaging component 23 is engaged in the engaging hole 35aa.

A rectangular through hole 36a that corresponds to the cross section of the principal portion of the operating section main unit 35 is formed in the slider 36, and, as a result of this through hole 36a being externally fitted onto the principal portion of the operating section main body 35, the slider 36 is mounted such that it cannot rotate but can move forwards and backwards in the longitudinal direction of the operating section main body 35, in other words, in the direction of the base end side axis La of the sheath 14. Moreover, as is shown in FIG. 3, an anchoring claw 36b is provided on the distal end side of the slider 36. In contrast, in a state in which the operating pipe 24 is fitted over the external circumference of the operating wire 12, the base end side of the operating wire 12 extends from the base end side aperture end of the sheath 14 through the through hole 20 inside the base 16, and further extends as far as the middle of the interior of the operating section main body 35, and is anchored integrally with the operating pipe 24 by the anchoring claw 36b of the slider.

Note that engaging holes 35c and 36c that are used for engaging the fingers of an operator are formed respectively in the operating section main body 35 and the slider 36, so that the slider 36 can be moved forwards or backwards relative to the operating section main body 35 using one hand.

Next, operations of the treatment tool for an endoscope according to the first embodiment that has the above described structure will be described.

Firstly, the insertion portion 101 of the endoscope 100 is inserted into an examination subject, and the distal end of this insertion portion 101 is moved forward to the vicinity of the portion being treated. Furthermore, the sheath 14 of this treatment tool 1 for an endoscope is inserted into the examination subject via the channel 103 that is formed in the endoscope operating section 102, and the treatment portion 10 of this distal end is moved forward as far as the portion being treated.

Next, the engaging ring 33b of the attachment 33 is engaged with the bottom end portion of the endoscope operating section 102. The connecting cord 30 that extends from a high frequency power supply is then connected to the plug 29.

Next, the sheath 14 is then pushed forwards slightly towards the distal end side, and the treatment portion 10 is made to protrude from the distal end of the endoscope insertion portion 101. In this state, the orientation of the treatment portion 10 relative to the portion being treated is adjusted. Namely, a determination is made, for example, from the screen of the endoscope as to whether or not the treatment portion is at an appropriate attitude relative to the portion being treated. If the attitude is not appropriate, the operating section 18 of the treatment tool 1 for an endoscope is rotated. When the operating section 18 is rotated, the base end portion of the operating wire 12 rotates integrally with the slider 36, and this rotation is transmitted to the distal end of the operating wire 12. As a result, the treatment portion 10 that is connected to the distal end of the operating wire 12 is rotated. When the treatment portion 10 has been rotated to a suitable position and been placed in a suitable attitude, the rotation of the operating section 18 is stopped.

Next, the slider 36 is operated so that the slider 36 is moved forwards or backwards and a predetermined treatment is performed on the portion being treated. For example, if the treatment portion 10 is the snare 10a, then after the position of the snare 10a has been adjusted so that it encircles the portion being treated, the slider 36 is moved backwards so that the portion being treated is clamped by the snare 10a. In this state, high frequency current is applied to the treatment portion 10 through the connecting cord 30, and the portion being treated is cauterized. As a result, the portion being treated is able to be removed.

Here, in the present embodiment, when the operating section 18 is rotated, because the base 16 can be fixed to the endoscope operating section 102 by the attachment 33, an operator is able to easily rotate the operating section 18 by holding it with one hand.

Note that the operation to fix the base 16 to the endoscope operating section 102 using the attachment 33 is not absolutely essential. For example, when the operating section 18 is rotated, if the base 16 is held by one hand and the operating section 18 is held and rotated by the other hand, the result is that it is possible to rotate the treatment portion 10, and it is not necessary to fix the base 16 to the endoscope operating section 102 using the attachment 33.

Moreover, in the present embodiment, the base 16 and the operating section 18 are placed in this order from the side closest to the sheath 14 along the base end side of the sheath 14. In addition, because the plug 29 is provided in the base 16 which is the fixed side when the operating section 18 is rotated, the connecting cord 30 that is connected to the plug 29 does not rotate and remains in a fixed state. As a result, it is difficult for the connecting cord 30 to become entangled with the rotated operating section 18.

Moreover, when the plug 29 and the attachment 33 protrude in opposite directions respectively from the base 16, and the treatment tool 1 for an endoscope is fixed by the attachment 33 to the endoscope operating section 102, the connecting cord 30 that is connected to the plug 29 extends on the opposite side from the attachment 33, namely, on the opposite side from the endoscope operating section 102, and the connecting cord 30 does not lie on top of the endoscope operating section 102. Because of this, an operator is able to easily verify the connection state between the plug 29 and the connecting cord 30, and is easily able to connect or disconnect the plug 29 and the connecting cord 30.

In addition, because the plug 29, the connecting cord 30 that is connected to the plug 29, and the attachment 33 are positioned on the same axis, even if tensile force is applied temporarily to the connecting cord 30 in the direction in which the contact portion with the plug 29 extends, this tensile force ends up acting in a straight line connecting the plug 29 with the engaging ring 33b of the attachment 33, which forms a rotation support point for the base 16. Because of this, there are no instances of moment acting accidentally on the base 16 causing it to rotate, so that, in this point as well, speedy operations using the operating section 18 are made possible.

Moreover, because the cylindrical component 25 that has suitable elasticity and is formed from an electroconductive material is interposed between the plug 29 and the operating pipe 24, excellent conductivity is secured between the plug 29 and the operating pipe 24 not only in a stationary state, as would be expected, but also during a forward or backward movement or rotational movement of the operating section 18. As a result, compared with when this type of component that has suitable elasticity and has electroconductivity is not used and conductivity is secured solely through the dimensional accuracy of components such as the plug and base and the like, it is not necessary to demand undue machining accuracy in components such as the plug 29 and the base 16.

Next, a variant example of the present embodiment will be given.

Figure 5:
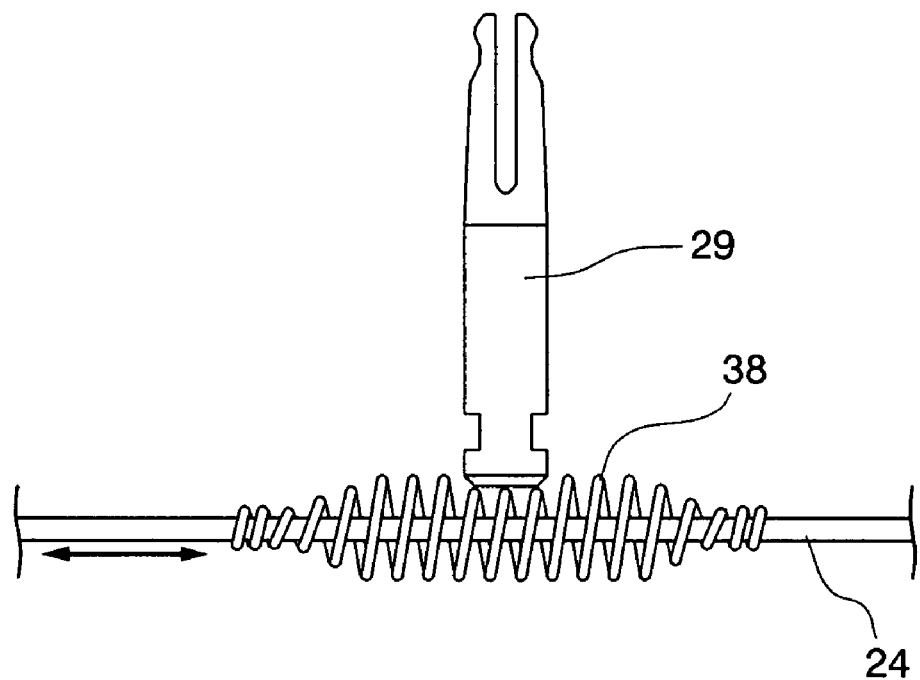
FIG. 5 is a side view showing principal portions of a variant example of the treatment tool for an endoscope according to the first embodiment of the present invention.

In the example shown in FIGS. 3 and 4 described above, the cylindrical component 25 that has suitable elasticity and is formed from an electroconductive material is interposed between the plug 29 and the operating pipe 24 in order to secure conductivity between the two, however, the present invention is not limited to this and, as is shown in FIG. 5, it is also possible to place a coil 38 that is formed from a metal conductive material around the external circumference of the operating pipe 24.

Figure 6:
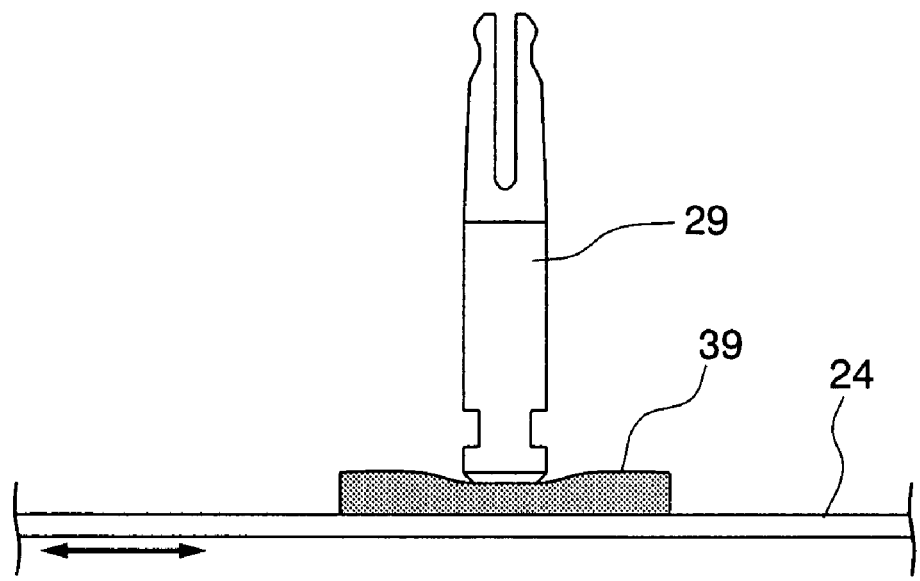
FIG. 6 is a side view showing principal portions of another variant example of the treatment tool for an endoscope according to the first embodiment of the present invention.

Moreover, as is shown in FIG. 6, it is also possible to interpose a sheet-shaped component 39 that has elasticity and is formed from an electroconductive material between the plug 29 and the operating pipe 24. In this case, if necessary, the sheet shaped component 39 may be adhered to the plug 29 or to the operating pipe 24 using an electroconductive adhesive agent.

Note that if the base 16, the connecting component 22 and the engaging component 23 are formed as a single unit, then assembly is simplified if the sheet shaped-component 39 is used instead of the cylindrical component 25.

Figure 7:
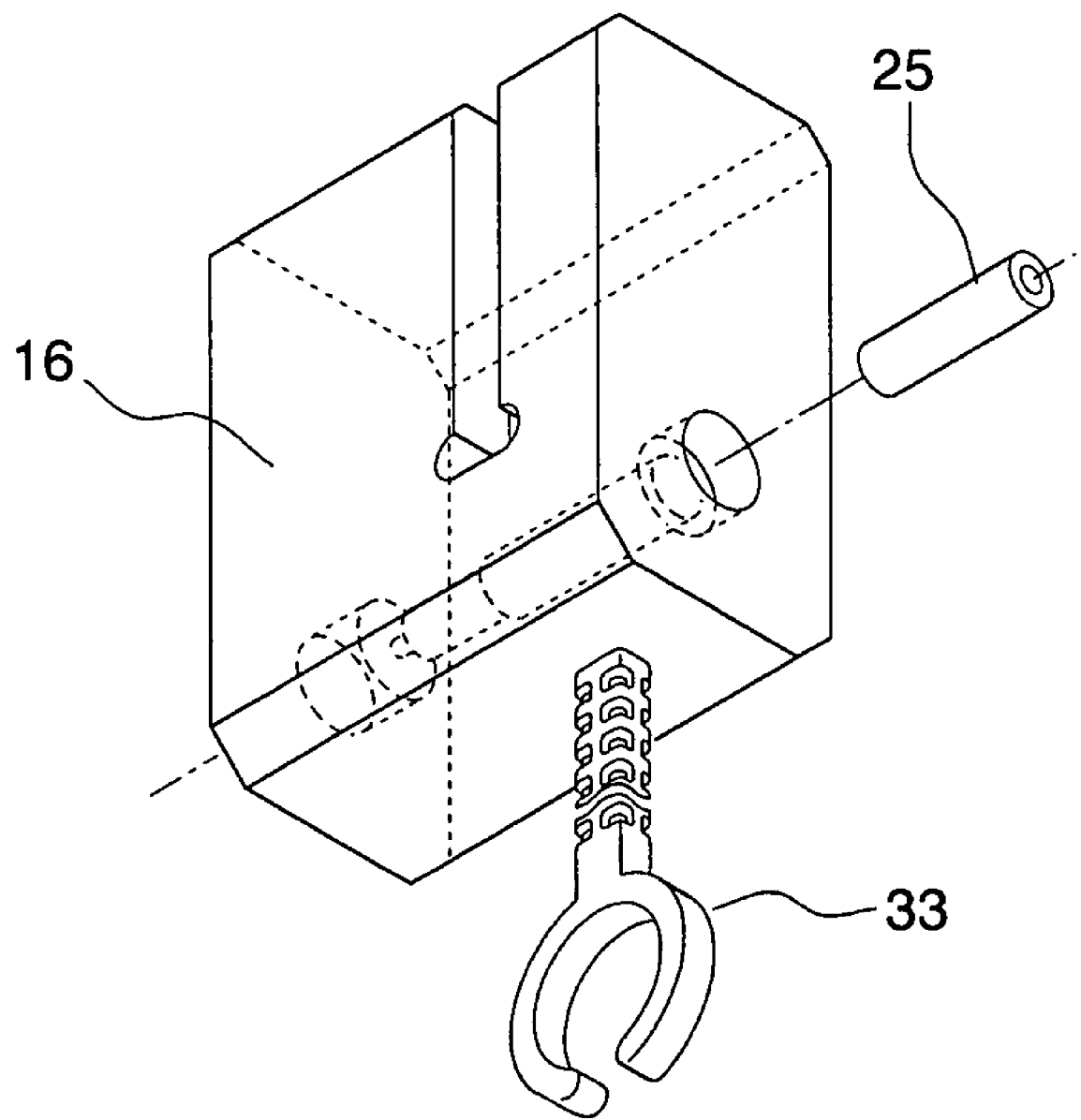
FIG. 7 is a perspective view showing principal portions of yet another variant example of the treatment tool for an endoscope according to the first embodiment of the present invention.

Moreover, in the example shown in FIGS. 3 and 4 described above, a structure is employed in which the attachment 33 is formed as a separate component from the base 16, and the attachment 33 is assembled with the base 16 by engaging the base end portion 33a of the attachment 33 in the attachment engagement groove 32 that is formed in the base 16. However, the present invention is not limited to this, and when the base 16 is molded from resin, as is shown in FIG. 7, the attachment 33 may also be molded integrally with the base 16.

[Second Embodiment]

Figure 8:
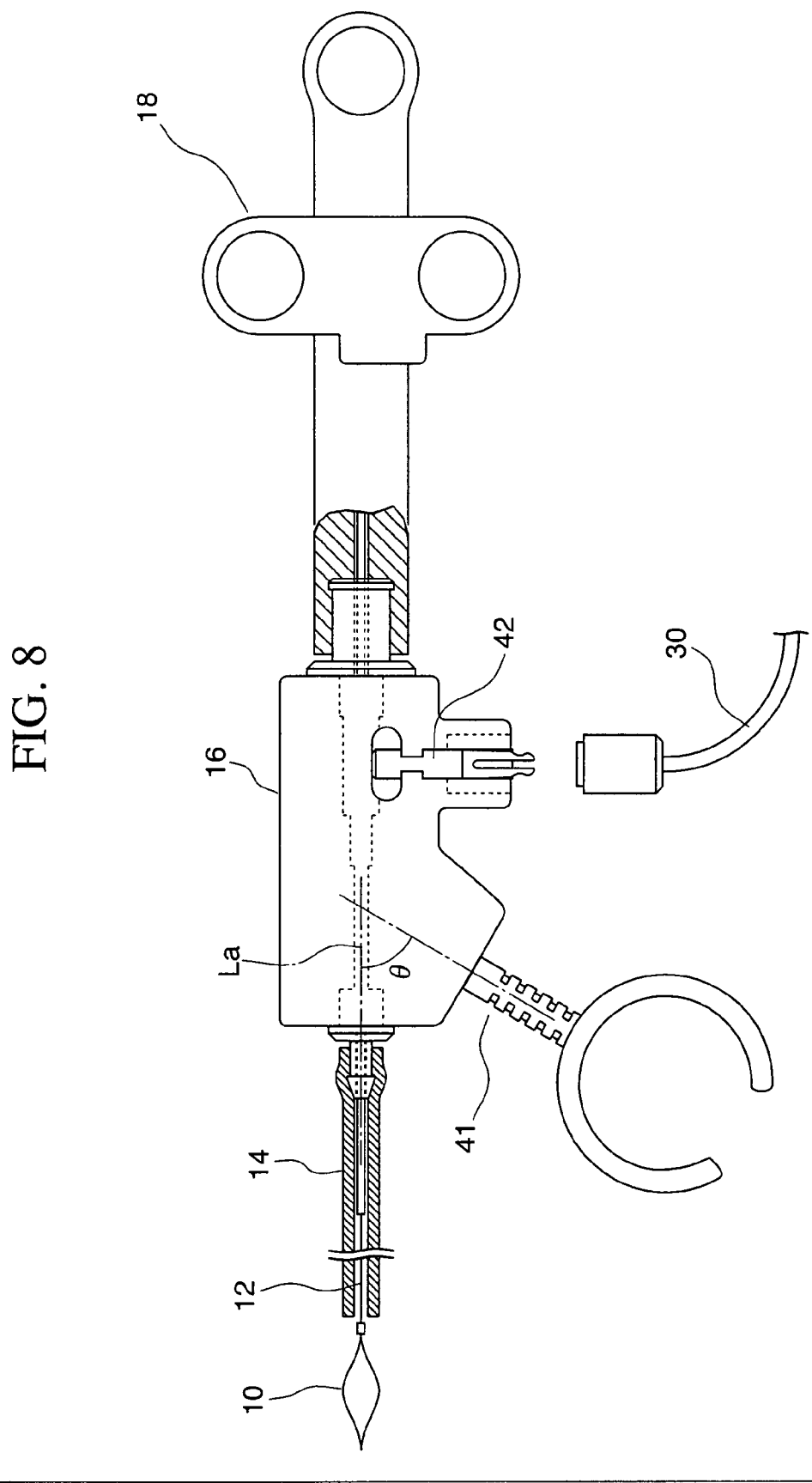
FIG. 8 is a partial cross-sectional view showing a treatment tool for an endoscope according to a second embodiment of the present invention.
Figure 10A:
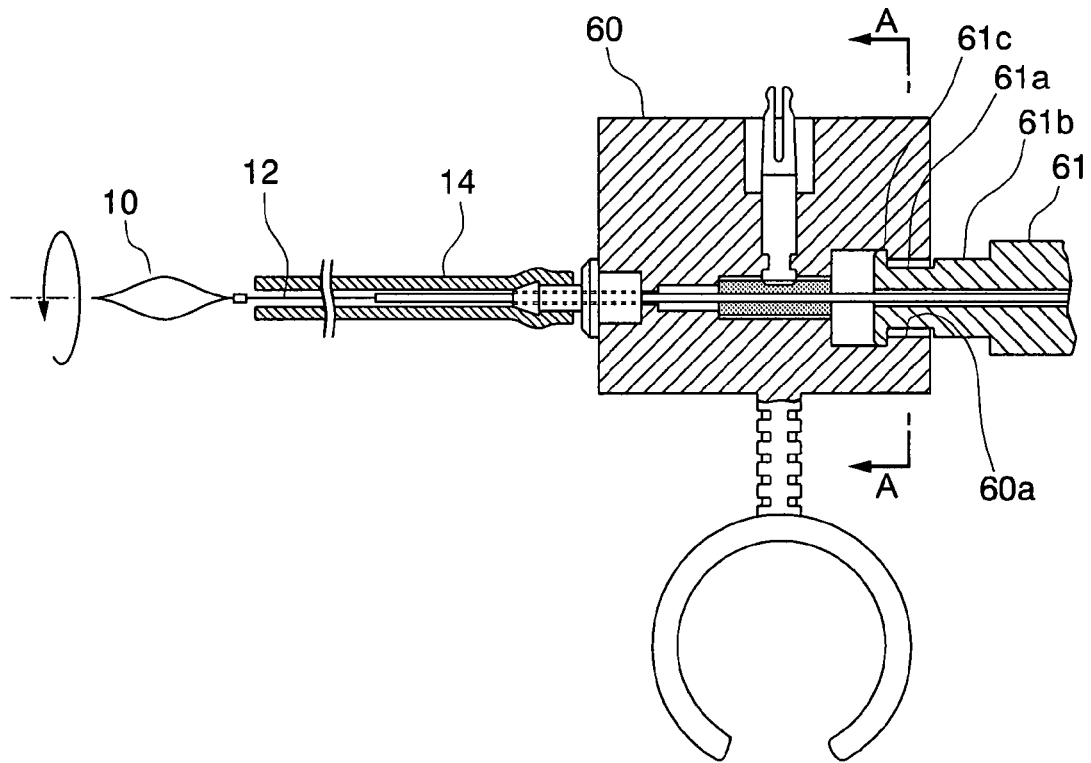
FIG. 10A is a cross-sectional view showing principal portions of a treatment tool for an endoscope according to a fourth embodiment of the present invention, and shows a state in which the treatment tool can be rotated.
Figure 10B:
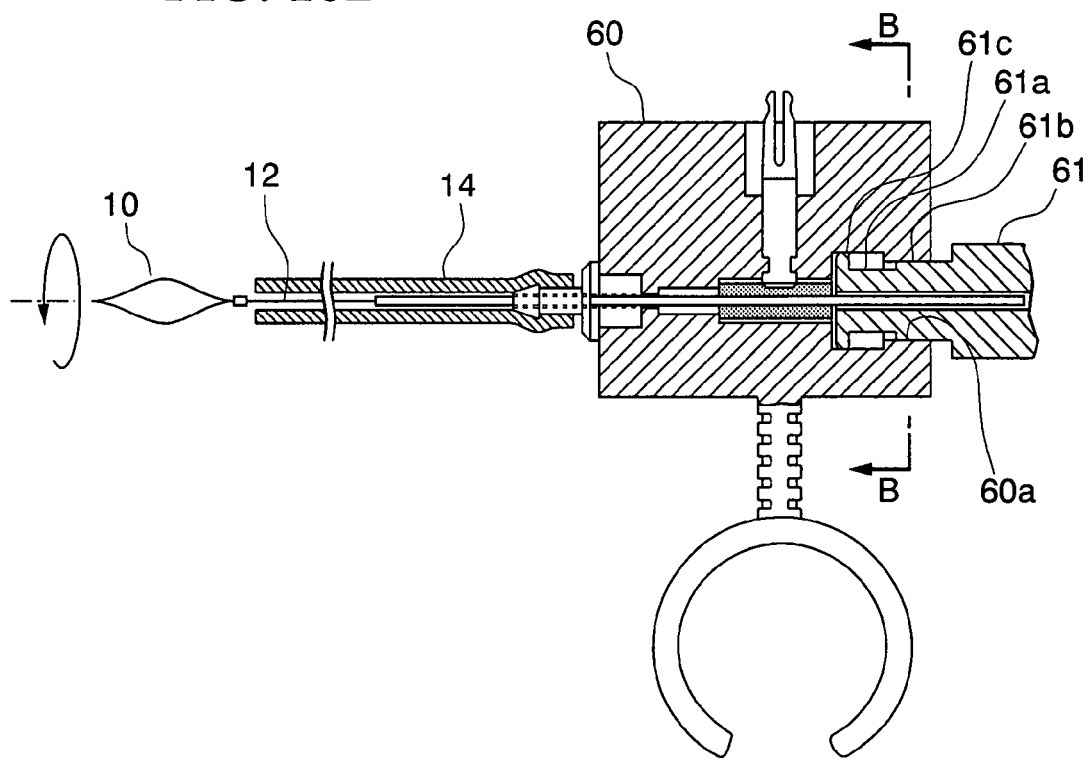
FIG. 10B is a cross-sectional view showing principal portions of a treatment tool for an endoscope according to a fourth embodiment of the present invention, and shows a state in which the treatment tool cannot be rotated.
Figure 11A:
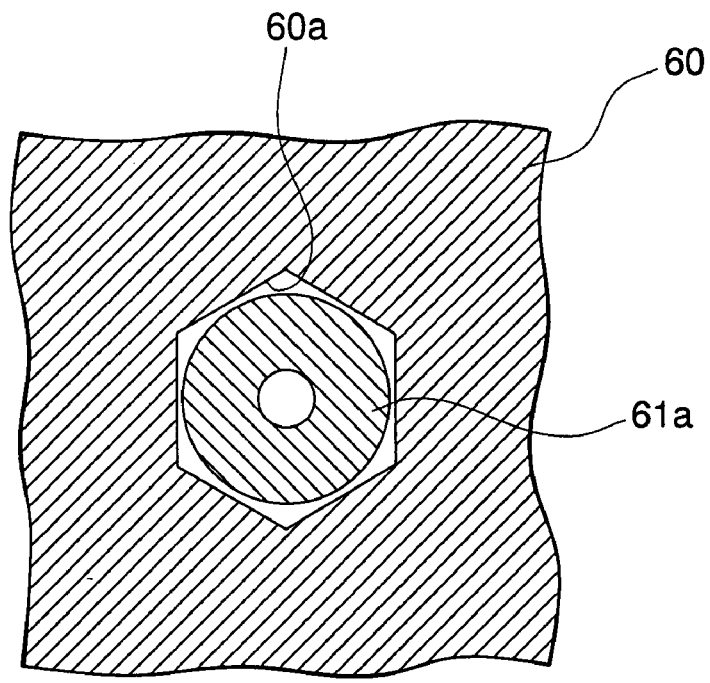
FIG. 11A is a cross-sectional view taken along a line A-A in FIG. 10A showing principal portions of a treatment tool for an endoscope according to a fourth embodiment of the present invention.
Figure 11B:
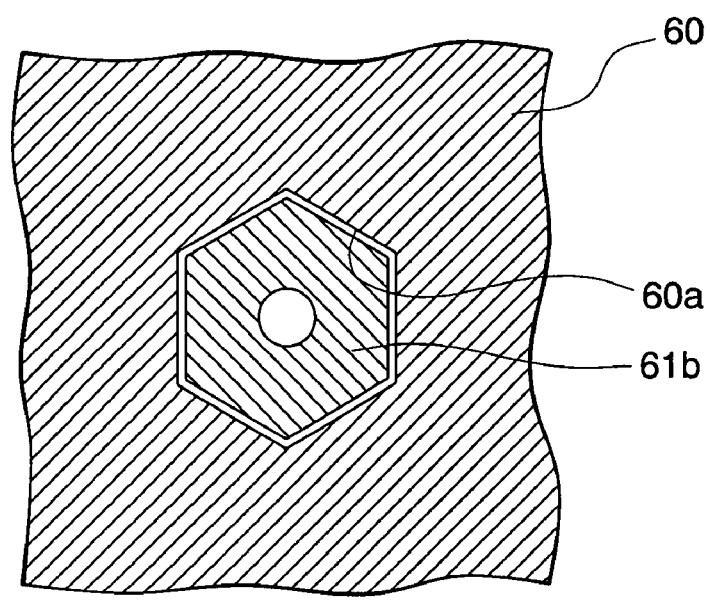
FIG. 11B is a cross-sectional view taken along a line B-B in FIG. 10B showing principal portions of a treatment tool for an endoscope according to a fourth embodiment of the present invention.

FIG. 8 shows principal portions of the treatment tool for an endoscope according to the second embodiment of the present invention.

Note that, for reasons of convenience, in the second embodiment, component elements that are the same as those in the first embodiment are given the same symbols and a description thereof is omitted. This also applies for the third and subsequent embodiments.

In the second embodiment, an attachment 41 and a plug 42 protrude in substantially the same direction from the base 16.

Namely, with the location where the operating wire 12 passes through the base 16 taken as the center, the attachment 41 and the plug 42 are both placed on one side thereof. The attachment 41 is placed at a predetermined acute angle of inclination θ (for example, 30 to 60 degrees) relative to the axis La on the base end side of the sheath 14, and the plug 42 is placed at an angle of approximately 90 degrees relative to the axis La on the base end side of the sheath 14.

In the treatment tool for an endoscope of this second embodiment, the connecting cord that is connected to the plug 42 extends on the attachment 41 side, namely, on the endoscope operating section side. Here, although a power supply cord or the like extends from the endoscope operating section, the connecting cord that is connected to the plug extends in the same direction substantially integrally with the power supply cord or the like that extends from this endoscope operating section. Because of this, managing the cords is easy.

[Third Embodiment]

FIG. 9 shows principal portions of the treatment tool for an endoscope according to the third embodiment of the present invention.

In the third embodiment, the fact that an attachment 51 and a plug 52 protrude in the same direction respectively from the base 16 is the same as in the second embodiment.

Here, both the attachment 51 and the plug 52 are placed at an angle of approximately 90 degrees relative to the axis La on the base end side of the sheath 14. Moreover, the plug 52 is placed closest to the sheath 14, while the attachment 51 is placed farthest from the sheath 14.

In the treatment tool for an endoscope of this third embodiment, it is possible to obtain the same effects as in the above described second embodiment.

[Fourth Embodiment]

FIG. 10A, FIG. 10B, FIG. 11A, and FIG. 11B show principal portions of the treatment tool for an endoscope according to the fourth embodiment of the present invention.

In the fourth embodiment, an aperture 60a that is provided in a side wall of an operating section main body 61 of a base 60 is formed in a regular polygon shape (for example, in a hexagonal shape). In contrast, the shape of a distal end portion of an operating section main body 61 that is inserted into this aperture 60a is formed such that a distal end small diameter portion 61a has a circular cross section whose diameter is smaller than the regular polygon shape, and a distal end large diameter portion 61b that is formed on the base end side of the small diameter portion 61a has a regular polygon-shaped cross section that corresponds to the aperture 60a. Note that 61c is a locking portion that is provided in the endmost point of the operating section main body.

In the treatment tool for an endoscope of this fourth embodiment, when rotating the operating section relative to the base 60, positioning in the axial direction of the operating section main body 61 relative to the base 60 is conducted such that the distal end small diameter portion 61a of the operating section main body 61 approaches a position corresponding to the aperture 60a portion. In this state, the operating section main body 61 is rotated.

When the rotation operation has been completed, if an operator desires to maintain the rotation position of the operating section main body 61 relative to the base 60, namely, if an operator desires to make the operating section main body 61 unable to rotate relative to the base 60, fine adjustment is made to the angle of the operating section main body 61 relative to the base 60 so that the distal end large diameter portion 61b coincides with the aperture 60a.

In this state, the operating section main body 61 is pushed towards the base 60 side, and the distal end large diameter portion 61b is engaged in the aperture 60a. As a result, the two corresponding peaks of the two regular polygons as well as the sides thereof become engaged with each other, and relative rotation between the base 60 and the operating section main body 61 becomes impossible.

Namely, in the fourth embodiment, it is possible to switch the operating section main body 61 as is desired between a state in which it is able to rotate relative to the base 60 and a state in which it is unable to rotate relative to the base 60.

[Fifth Embodiment]

FIG. 12 shows principal portions of the treatment tool for an endoscope according to the fifth embodiment of the present invention.

In the fifth embodiment, the direction of an engaging ring 71a of an attachment 71 is different in comparison with the above described first embodiment.

Namely, in the above described first embodiment, a surface created by the engaging ring of the attachment is parallel to the axis La on the base end side of the sheath 14, however, in this fifth embodiment, a surface S created by the engaging ring 71a of the attachment 71 is orthogonal to the axis La on the base end side of the sheath.

In this case, when a tool for an endoscope is fixed by the attachment 71 to the endoscope operating section, the axis La on the base end side of the sheath 14 is positioned so as to be parallel with an axis Lb of the endoscope operating section 102.

[Sixth Embodiment]

Figure 13:
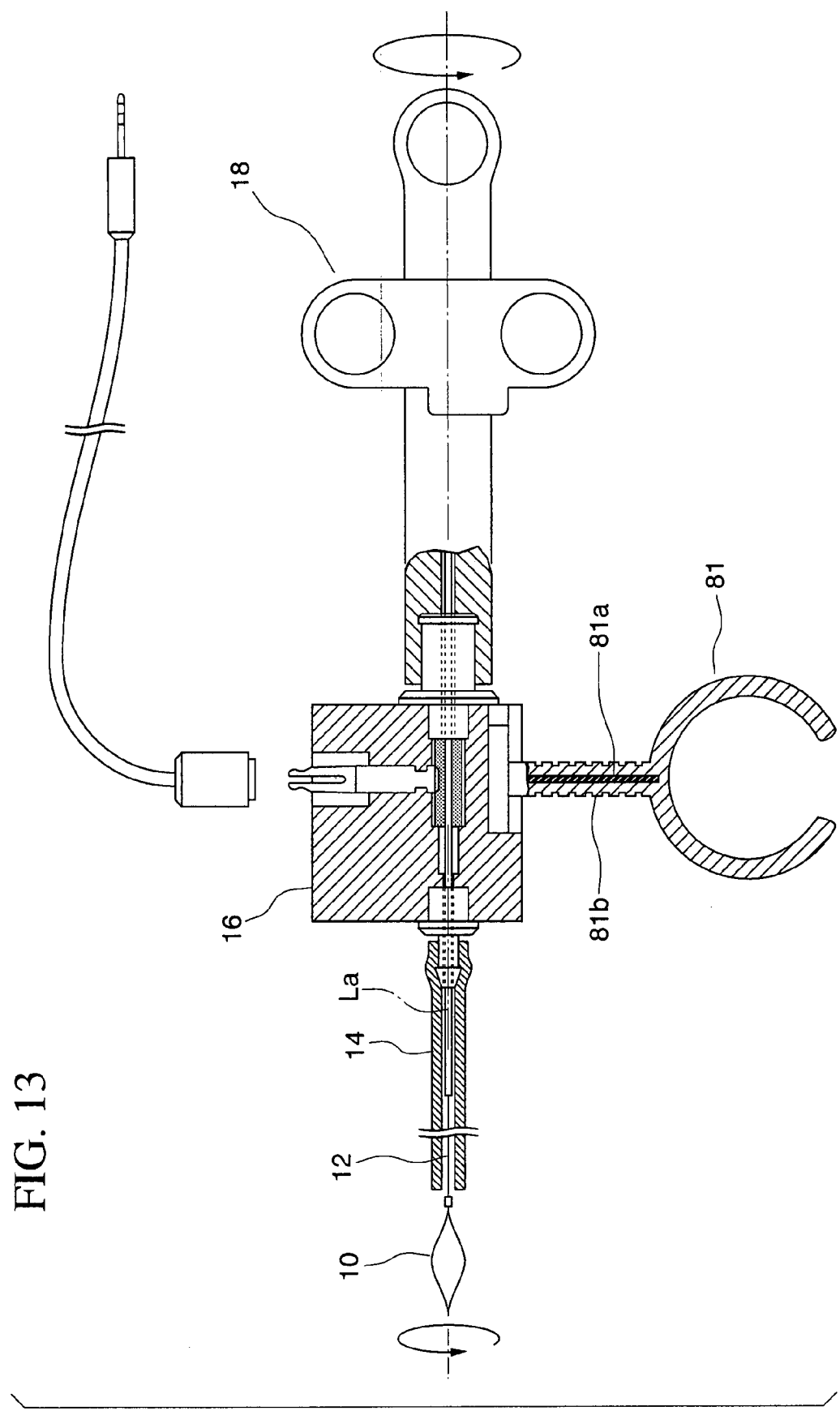
FIG. 13 is a partial cross-sectional view showing a treatment tool for an endoscope according to a sixth embodiment of the present invention.
Figure 14A:
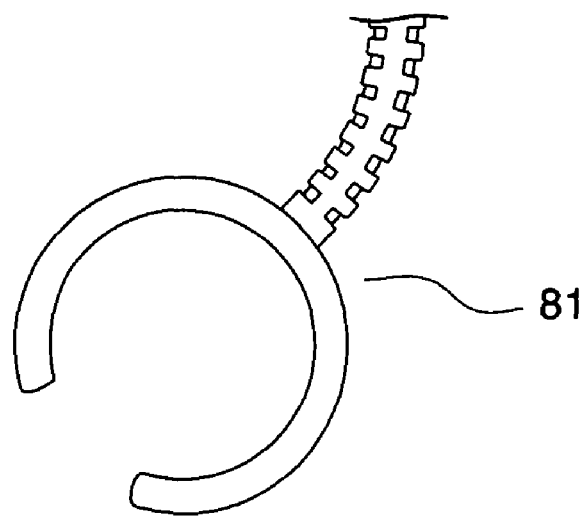
FIG. 14A is a perspective view showing principal portions of an attachment and illustrates an action of the treatment tool for an endoscope according to the sixth embodiment of the present invention.
Figure 14B:
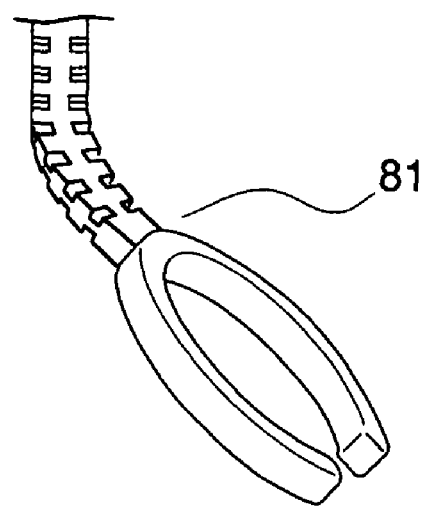
FIG. 14B is a perspective view showing principal portions of an attachment and illustrates an action of the treatment tool for an endoscope according to the sixth embodiment of the present invention.

FIG. 13, FIG. 14A, and FIG. 14B show principal portions of the treatment tool for an endoscope according to the sixth embodiment of the present invention.

In the sixth embodiment, a metal rod 81a that is formed from a deformable material and in an easily deformable shape is embedded in a central shaft portion of an attachment 81, and the external circumference of the attachment 81 is covered by a soft resin 81b.

In this embodiment, as is shown in FIG. 14A and FIG. 14B, it is possible using the plastic deformation of the rod 81a, which is formed from a metal material, to freely set the mounting angle of the attachment relative to the endoscope operating section.

[Seventh Embodiment]

Figure 15:
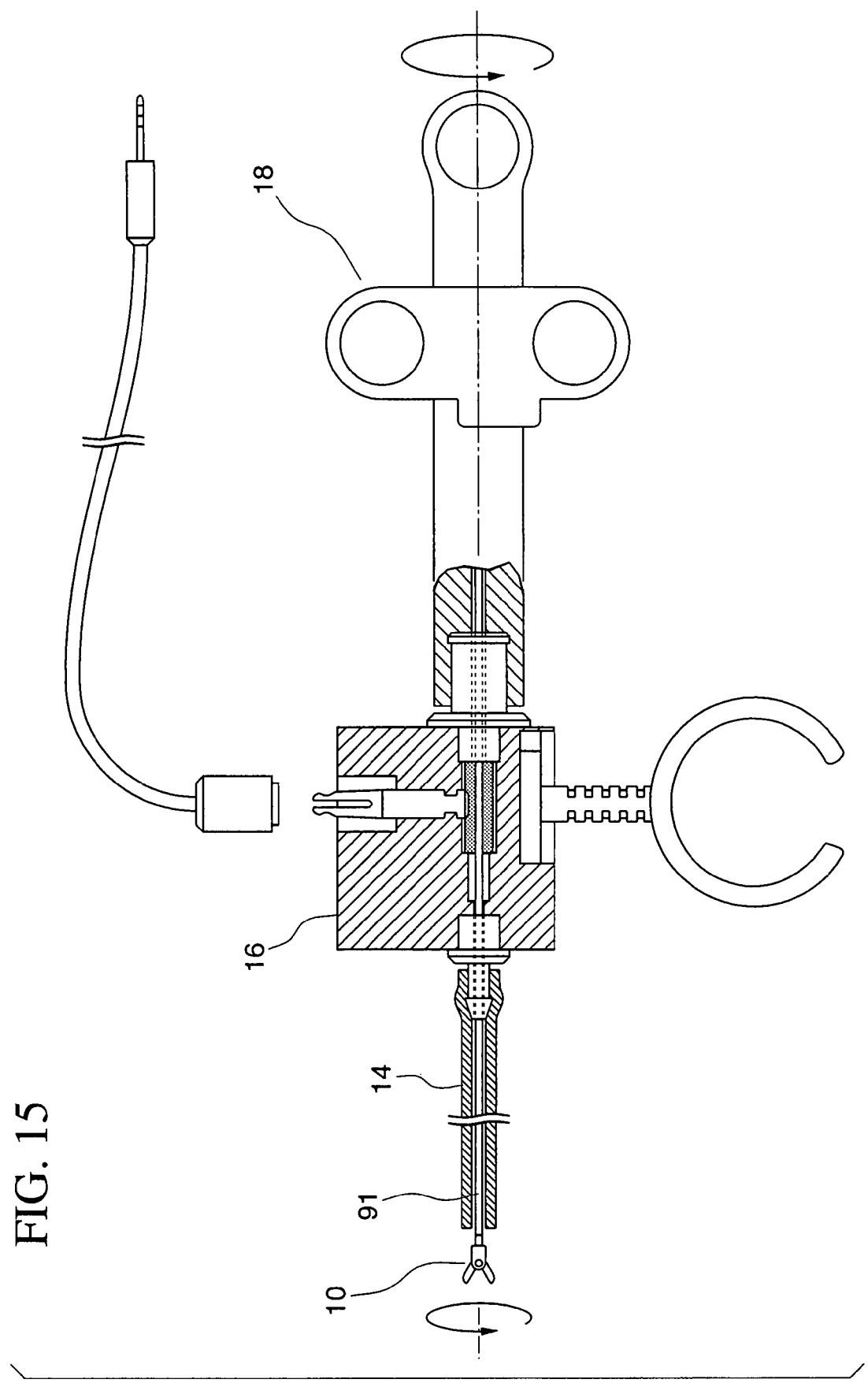
FIG. 15 is a partial cross-sectional view showing a treatment tool for an endoscope according to a seventh embodiment of the present invention.

FIG. 15 shows principal portions of the treatment tool for an endoscope according to the seventh embodiment of the present invention.

In this seventh embodiment, an example is shown in which hot biopsy forceps 91 are used as an example of a treatment portion. Namely, by supplying a high frequency current to a spherical cup portion via the operating wire 12, it is possible to perform an excision and stop bleeding simultaneously, and it is also possible for the present invention to be applied in this type of treatment portion as well.

The treatment tool for an endoscope of the present invention includes: a treatment portion that is positioned on a distal end side and of which at least a portion is formed from an electroconductive material; an operating wire that is formed from an electroconductive material and is connected to the treatment portion; a sheath that is formed from an electrically non-conductive material through which the operating wire is inserted; a base that is fixed to a base end side of the sheath; an operating section that is rotatably mounted on the base and is connected to a base end side of the operating wire, and that causes the treatment portion to move forwards and backwards and to rotate via the operating wire; and a plug that is provided on the base and is electrically connected to the operating wire.

In this treatment tool for an endoscope, because a plug is provided on the base which is the side that is fixed during operations performed using the operating section, and because a connecting cord extends from this plug, during a forward or backward movement or during a rotational movement by this operating section, the connecting cord does not become entangled with the operating section and excellent operability can be secured.

Moreover, in the treatment tool for an endoscope according to the present invention, the operating section is provided with an operating section main body that is rotatably attached to the base, and a slider that is attached such that the slider can move forwards or backwards relative to the operating section main body, and a base end side of the operating wire is connected to the slider.

In this treatment tool for an endoscope, if the slider is moved forwards or backwards relative to the operating section main body, the operating wire also moves in an axial direction in conjunction with the movement of the slider, and the treatment portion that is attached to the distal end is operated in conjunction with this movement of the operating wire.

Moreover, in the treatment tool for an endoscope according to the present invention, an attachment that can be attached to or removed from an endoscope operating section is attached to the base.

In this treatment tool for an endoscope, the base can be mounted via the attachment on the endoscope operating section. As a result, when rotating the treatment portion, it is sufficient for an operator to rotate it holding only the operating section without having to support the base. Namely, using this treatment tool for an endoscope an operator is able to perform a rotation operation using only one hand.

Moreover, in the treatment tool for an endoscope according to the present invention, an electroconductive elastic component is interposed between a base end side of the plug and the operating wire.

In this treatment tool for an endoscope, by pushing the plug towards the operating wire side using a certain amount of pushing force, it is possible to secure excellent conductivity between the plug and the operating wire not only in a stationary state, as would be expected, but also during a rotational movement or forward or backward movement of the operating section. As a result, compared with when an electroconductive component is not used and conductivity is secured solely by the dimensional accuracy of components such as the plug and base and the like, it is not necessary to demand undue machining accuracy in components such as the plug and the base.

Moreover, in the treatment tool for an endoscope according to the present invention, the plug and the attachment protrude in the same direction from the base.

In this treatment tool for an endoscope, the connecting cord that is connected to the plug extends towards the attachment side, namely, towards the endoscope operating section side. Normally, an operator is, in many cases, present on the opposite side from the endoscope operating section and, in this case, the connecting cord does not extend on the operator's side so that, for this reason as well, operability is excellent.

Moreover, in the treatment tool for an endoscope according to the present invention, the plug and the attachment protrude in mutually opposite directions from the base.

In this treatment tool for an endoscope, because the connecting cord that is connected to the plug extends on the opposite side from the endoscope operating section side, the connecting cord does not lie on top of the endoscope operating section. Because of this, an operator is able to easily verify the connection state between the plug and the connecting cord, and is easily able to connect or disconnect the plug and the connecting cord.

Moreover, in the treatment tool for an endoscope according to the present invention, the base is attached to the base end side of the sheath, and the operating section main body is mounted on the opposite side of the base from the sheath so as to be able to rotate around a base end side axis of the sheath, and the slider is mounted on the operating section main body so as to be able to move forwards or backwards in the direction of the base end side axis of the sheath, and the base end side of the operating wire extends from an aperture end on the base end side of the sheath through the base towards the operating section main body side, and is connected to the slider.

In this treatment tool for an endoscope, the base and the operating section are placed in this order from the side closest to the sheath 14. In addition, because the plug is provided in the base, the connecting cord that is connected to the plug does not become entangled with the operating section even when the operating section is rotated.

According to the present invention, because a plug is provided on the base which is the side that is fixed during operations performed using the operating section, and because a connecting cord extends from this plug, during a forwards or backwards movement or during a rotational movement by this operating section, the connecting cord does not become entangled with the operating section and excellent operability can be secured. Moreover, when the base is connected to and supported by the endoscope operating section via the attachment, it is sufficient for an operator to operate only the operating section and this operation can be performed using only one hand.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

The invention claimed is:

1. A treatment tool for an endoscope comprising:
 a treatment portion that is positioned on a distal end side and of which at least a portion is formed from an electroconductive material;
 an operating wire that is formed from an electroconductive material and is connected to the treatment portion;
 a sheath that is formed from an electrically non-conductive material through which the operating wire is inserted;
 a base being comprised of a base main body having a connecting arm, the base being fixed to a base end side of the sheath so as to be orthogonal to an axis line of the sheath by means of the connecting arm;
 an operating section being provided with an operating section main body that is rotatably attached to the base main body and to a slider that is attached to the operating section main body so that the slider can move forwards or backwards relative to the operating section main body, and a base end side of the operating wire that is connected to the slider, the operating section causing the treatment portion to move forwards and backwards and to rotate via the operating wire; and
 a plug that is provided on the base main body and is electrically connected to the operating wire, wherein
 the slider is attached to the operating section main body so that a direction in which the slider moves is orthogonal to an axis line which connects the base and the axis line of the sheath and so that an axis line along the direction in which the slider moves and the axis line of the sheath form skew axis lines.

2. The treatment tool for an endoscope according to claim 1, wherein an attachment that can be attached to or removed from an endoscope operating section is attached to the base.

3. The treatment tool for an endoscope according to claim 2, wherein the plug and the attachment protrude in the same direction from the base.

4. The treatment tool for an endoscope according to claim 2, wherein the plug and the attachment protrude in mutually opposite directions from the base.

5. The treatment tool for an endoscope according to claim 1, wherein an electroconductive elastic component is interposed between a base end side of the plug and the operating wire.

6. The treatment tool for an endoscope according to claim 1, wherein the base is attached to the base end side of the sheath, and the operating section main body is mounted on the opposite side of the base from the sheath so as to be able to rotate around a base end side axis of the sheath, and the slider is mounted on the operating section main body so as to be able to move forwards or backwards in the direction of the base end side axis of the sheath, and the base end side of the operating wire extends from an aperture end on the base end side of the sheath through the base towards the operating section main body side, and is connected to the slider.

* * * * *